United States Patent [19]

Brychta et al.

[11] Patent Number: 4,691,700
[45] Date of Patent: Sep. 8, 1987

[54] ANAESTHETICAL CIRCUIT WITH REVERSE INHALATION EQUIPPED WITH AN INJECTOR OF ESCAPED ANAESTHETICS

[75] Inventors: Ondrej Brychta; Jozef Tlucko; Viktor Magdolen; Miroslav Brostik, all of Trencin; Dusan Klimacek, Stara Tura, all of Czechoslovakia

[73] Assignee: Konstructa Trencin, narodny podnik, Trencin, Czechoslovakia

[21] Appl. No.: 870,140

[22] Filed: Jun. 2, 1986

[51] Int. Cl.$^4$ ............................................. A61M 16/00
[52] U.S. Cl. .......................... 128/200.21; 128/204.26; 128/205.24; 128/910; 128/203.28; 128/205.15
[58] Field of Search ...................... 128/203.28, 204.25, 128/204.26, 205.15, 205.17, 205.24, 200.18, 200.21, 203.14, 910

[56] References Cited

U.S. PATENT DOCUMENTS 1,737,575 12/1929 Drager ........................... 128/203.28
3,901,230 8/1975 Henkin ........................... 128/215.17
4,596,246 6/1986 Lyall ............................... 128/203.28

FOREIGN PATENT DOCUMENTS 1501550 10/1967 France ........................... 128/205.15
1374582 11/1974 United Kingdom ........... 128/205.15
2062476 5/1981 United Kingdom ........... 128/205.24

Primary Examiner—Henry J. Recla

[57] ABSTRACT

An improved anaesthetical circuit with reverse inhalation is equipped with an injector of escaped anaesthetics connected by an inlet pipe to a valve in which a feeding pipe, leading from a source of constant flow, discharges a signal from a differential pressure indicator, being led into the valve through a conduit. The differential pressure indicator is fed from an energy source, on one hand, together with a conduit pipe leading from a drive pipe into the pressurized chamber of the differential pressure indicator, and a pipe leading from a connection pipe into the vacuum chamber of the differential pressure indicator, on the other hand. A connection pipe connecting an outlet pipe of the injector through a check valve with a rubber bag, which is arranged in a cylinder attached to the anaesthetical circuit. A drive pipe leading into the cylinder, containing the rubber bag and a pipe, leading from the drive pipe, leads into a control chamber of an expiration valve, the outlet pipe of which leads into a distribution valve. The distribution valve has two branches, one branch of it forming an exhaust system provided by a check valve leading out from the anaesthetical circuit, and the second branch of the distributor valve forming a runback pipe which is equipped with a pressurized valve which is connected through a carbon dioxide absorber and through a check valve to the connection pipe leading into the vacuum chamber.

7 Claims, 1 Drawing Figure

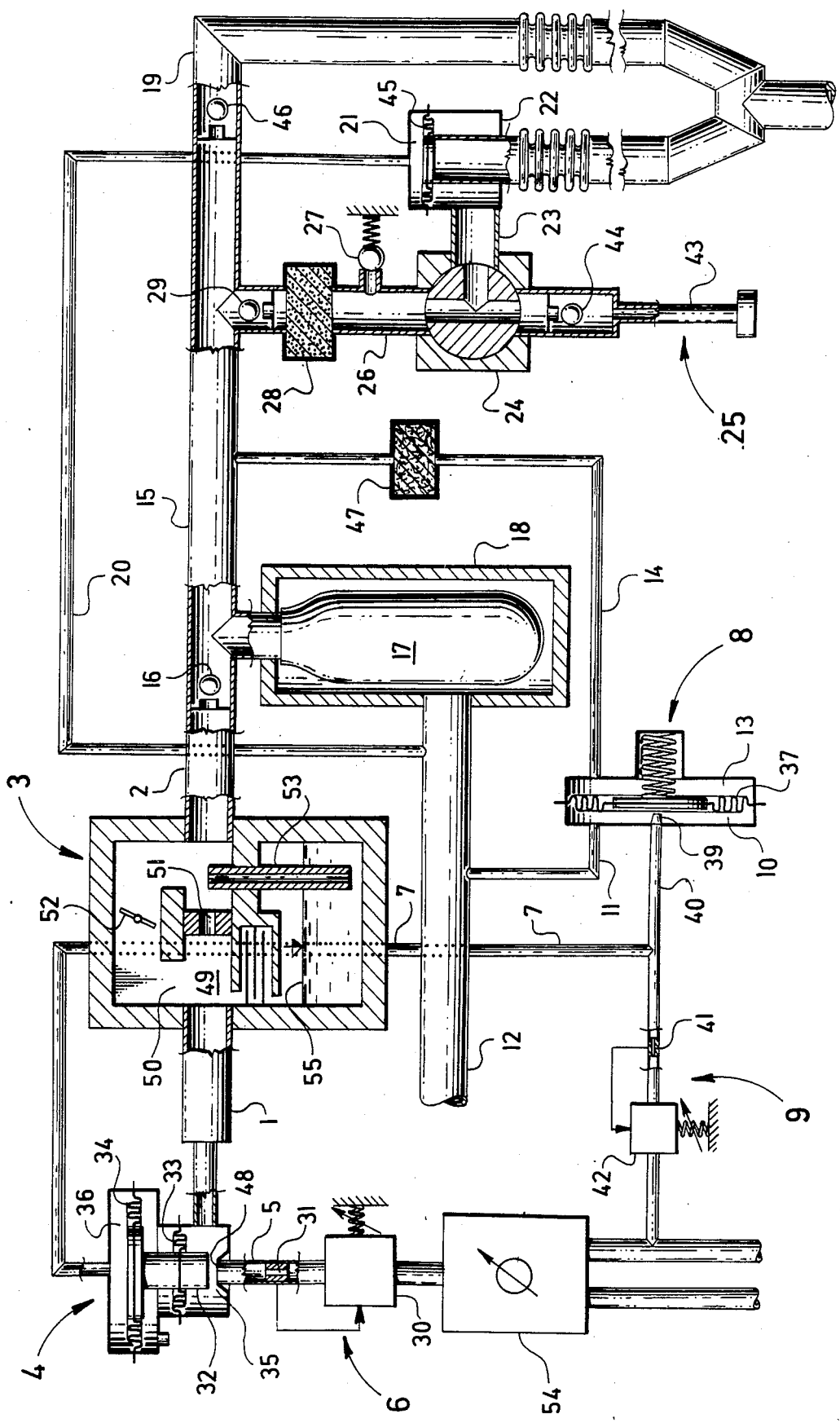

ANAESTHETICAL CIRCUIT WITH REVERSE INHALATION EQUIPPED WITH AN INJECTOR OF ESCAPED ANAESTHETICS

FIELD OF THE INVENTION

The invention concerns anaesthetical circuit with reverse inhalation equipped with an injector of escaped anaesthetics.

DESCRIPTION OF THE PRIOR ART

Prior known devices for applying total anaesthesia are either anaesthetical circuits with reverse inhalation equipped with quantitative and thermally compensated evaporators of escaped anaesthetics, or secondly, anaesthetical circuits without reverse inhalation and with injectors of escaped anaesthetics.

A prior known art of the first type concerns a circuit where most of the expired gases recirculate in the circuit, and the volume of the escape gases is continually refilled by an anaesthetical gas mixture containing a gaseous phase of an escape anaesthetic, for example, narcothane, the concentration of which in the gas mixture is programmed by a quantitative and thermally compensated evaporator.

The most complex part of this circuit is represented by the evaporator of escaped anaesthetics which maintains the programmed concentration of anaesthetic in the carrier gas independently of the instantaneous flow of gases through the evaporator, and independently of the temperature variations outside and inside of the evaporator. The independence of the resulting concentration on temperature variations is solved either by an automatic thermal compensating apparatus, or by the mass of the evaporator which forms a sufficiently great thermal delay. This makes possible to compensate the temperature manually according to a thermometer inside of the evaporator, and according to compensation curves of the hand-operated compensation apparatus.

In the case of an automatic thermal compensation, the evaporator represents a device having a relatively intricate and complex technological design which demands regular checking after a certain operation time. This checking consists of professional testing and adjusting of the thermal compensation apparatus.

In the case of an evaporator equipped with a hand-operated compensation apparatus, the design of the evaporator is characterized by a relatively great sturdiness and mass, the disadvantage being the need to check the temperature in the evaporator by an operator, and to constantly correct it when the temperature changes.

Anaesthetical devices having both evaporator types of escaped anaesthetics make possible to design circuits with reverse inhalation what substantialy reduces the consumption of escaped anaesthetics and the contamination of operation theatres used by anaesthetics.

Prior known arts of the second types concerns an open circuit where all expired gases flow from the ventilation circuit into a exhausting apparatus. Only fresh gases saturated with fresh vapors of anaesthetic supplied in the circuit by an injector flow in the circuit. The injector represents the relatively simple apparatus, which injects the escaped anaesthetic in its liquid phase only during a given flow of anaesthetical gases, independently on the momentary consumption of gases in the circuit. The disadvantage of this apparatus is a relatively high consumption of liquid anaesthetic. A further disadvantage of the device is the fact that the cycling mechanism forms an integral part of the ventilator that ventilates the device. The cycling mechanism cannot be used for another ventilator, or for handoperated drive, or even for a spontaneous ventilation, without a special ventilator.

SUMMARY OF THE INVENTION

The shortcomings of both cited anaesthetical circuits, are remedied by the present anaesthetical circuit with reverse inhalation equipped with an injector of escaped anaesthetic.

The objects of overcoming the shortcomings of the prior arts are met by a circuit design in which an injector is connected by means of an inlet pipe to a valve in which a feeding pipe, leading from a source of constant flow, is discharged a signal from a differential pressure indicator, being led into the said valve through a conduit. The differential pressure indicator being fed from an energy source, on one hand, together with a conduit pipe leading from a drive pipe into the pressurized chamber of the differential pressure indicator, and a pipe leading from a connection pipe into the vacuum chamber of the differential pressure indicator, on the other hand. A connection pipe connecting an outlet pipe of the said injector through a check valve with a rubber bag, which is arranged in a cylinder attached to the anaesthetical circuit. A drive pipe leading into the said cylinder, containing the said rubber bag and a pipe, leading from the said drive pipe, leads into a control chamber of an expiration valve, the outlet pipe of which leads into a distribution valve. The distribution valve has two branches, one branch of it forming an exhaust system provided by a check valve leading out from the anaesthetical circuit, and the second branch of the distributor valve forming a runback pipe which is equipped with a pressurized valve in which is connected through a carbon dioxide absorber and through a check valve to the said connection pipe leading into the vacuum chamber.

The objects of the present invention are further met by the fact that the source of constant flow is formed by a pressure regulator, a feeding pipe of which is equipped with a calibrated opening.

The objects of the present invention are further met by the fact that an automatic gas mixture is connected to the source of the constant flow.

The objects of the present invention are further met by the fact that the valve is formed by a movable part assembled of a membrane having a smaller effective surface and of a membrane having a bigger effective surface separating a through flow chamber of the valve from a control chamber of the valve, the signal being lead into the control chamber by the conduit.

The objects of the present invention are further met by the fact that the differential pressure indicator is formed by a membrane separating the pressurized chamber from the vacuum chamber. The membrane in the vacuum chamber, being in contact with a spring, and a membrane seat being arranged under the center of the membrane forming an exhaust opening of a pressure divider. The pressure divider is formed by a pipe with a feeding opening, the pipe being connected to a energy source formed by a pressure regulator, and the conduit of the signal being discharged from the pipe between the membrane seat and the feeding opening.

The objects of the present invention are further met by the fact that the exhaust system leading out from the anaesthetical circuit contains a pipe, the a diameter and the length of which forms a resistance. This resistance is equal to the sum of the resistances of runback pipe, the carbon dioxide absorber, the check valve, the rubber bag, and the drive pipe.

The objects of the present invention are further met by the fact that the injector is provided by a main channel having a calibrated opening behind which a capillary tube with an anaesthetic is discharged, and parallel channel to the main channel being provided by an adjustable throttle element.

The improved operation of the invention results from the connection of the injector of a escaped anaesthetics with an anaesthetical circuit equipped with a reverse inhalation by means of a differential pressure indicator whose signals start and stop a constant flow of the mixture of anaesthetical gases through the injector, and into the rubber bag forming a gas container of the anaesthetical circuit. The constant flow of the gas mixture in the pulse has such a value which is, on the one hand, sufficient for quick evaporation of the escaped anaesthetic supplied by the injector and, on the other hand, simultaneously sufficient for forming of the defined energy being necessary for the injection of the anaesthetic through the capillary tube of the injector. The energy which is necessary for the injection of the liquid anaesthetic through the capillary tube is given by the pressure gradient on the throttle element of the injector by means of which the desired concentration of the escaped anaesthetic in anaesthetical gases is adjusted.

BRIEF DESCRIPTION OF THE DRAWINGS

An example of the anaesthetic circuit with reverse inhalation equipped with an injector of escaped anaesthetic according to the invention is shown in FIG. 1.

DETAILED SPECIFICATION

Referring now to FIG. 1, an injector 3 is connected by means of an inlet pipe 1 to a valve 4 and a feeding pipe 5 leading from a source 6 of constant flow to be discharged in the valve 4. A signal from a differential pressure indicator 8 is lead into the valve 4 through a conduit 7, the differential pressure indicator 8 being fed from an energy source 9. A pipe 11 leads from a drive pipe 12 into the pressurized chamber 10 of the differential pressure indicator 8. A pipe 14 leads from a connection pipe 15 into the vacuum chamber 13 of the differential pressure indicator 8, the connection pipe 15 connecting an outlet pipe 2 of the injector 3 through a check valve 16 with a rubber bag 17 arranged in a cylinder 18. The outlet pipe 2 is through the check valve 16 also connected to the anaesthetical circuit 19. The pipe 14 is equipped with a bacteriological filter 47. The drive pipe 12 leads into the cylinder 18. A pipe 20 leads from the drive pipe 12 into a control chamber 21 of an expiration valve 22 having a membrane 45. An outlet pipe 23 of the expiration valve 22 leads into a divider valve 24. Its one branch forms an exhaust system 25 equipped with a check valve 44 leading out from the anaesthetical circuit. The second branch of the divider valve 24 forms a runback pipe 26 equipped with a pressurized valve 27, the second branch being connected through a carbon dioxide absorber 28 and through a check valve 29 to the connection pipe 15.

The injector 3 contains a main channel 49 connected to the inlet pipe 1. A calibrated opening 51 is arranged in the main channel 49. A capillary tube 53 leading from under the level of the liquid anaesthetic 55 is discharged behind the calibrated opening 51. The space over the level of the liquid anaesthetic 55 is, for the reason of pressure equalizing, connected with the main channel 49, e.g. through a labyrinth. A parallel channel 50 is arranged in the injector 3 parallel that is to the main channel 49, the parallel channel 50 being equipped with an adjustable throttle element 52.

The source 6 of constant flow is formed by a pressure regulator 30 which is equipped with defeating pipe 5 having a calibrated opening 31. The valve 4 having a seat 48, is formed by a movable part 32 assembled from membranes 33, 34. The membrane 33 has a smaller effective surface, and the membrane 34 has a bigger effective surface and separates a through flow chamber 35 from a control chamber 36 of the valve 4, the signal being lead into the control chamber 36 through the conduit 7.

The differential pressure indicator 8 is formed by a membrane 37 separating the pressurized chamber 10 from the vacuum chamber 13. The membrane 37 is in the vacuum chamber 13 in contact with a spring 38. A membrane seat 39 is discharged in the pressurized chamber 10 under the center of the membrane 37, the membrane seat 39 forming a exhaust opening of a pressure divider formed by a pipe 40 with a feeding opening 41. The pipe 40 is connected to the energy source 9 formed by a pressure regulator 42. The conduit 7 of the signal is discharged from the pipe 40 between the membrane seat 39 and the feeding opening 41.

The exhaust system 25 leading from the anaesthetical circuit 19 is formed by a pipe 43, the diameter in length of which forms a resistance. This resistance being comparable with the sum of resistances of the runback pipe 26, the carbon dioxide absorber 28, the check valve 29, the rubber back 17, and of the drive pipe 12.

The operation of the anaesthetical circuit with reverse inhalation equipped with an injector of escaped anaesthetics, according to the invention, is explained further according to the description of the example shown in the drawing. The operation of the device must comply with a spontaneous ventilation of the patient's lungs, or with a hand-operated ventilator and with a control ventilation of the patient's lung.

During the spontaneous ventilation of the patient, the drive pipe 12 is connected to the surrounding atmosphere either by means of a self-expanding bag equipped with a patient's valve, or by means of a ventilation circuit of a ventilator used for this purpose, its automatic operation being switched off. The ventilation circuit of the ventilator makes it posible to execute a spontaneous ventilation with or without inhalation assistance, eventually with a pressure indicator 8. This is not shown in the drawing. During a spontaneous inhalation of the patient, the vacuum in the anaesthetical circuit 19 closes by means of the membrane 45, its seat in the expiration valve 22. The vacuum opens the check valve 46 and is transferred through the connection pipe 15, through the check valve 29 and the carbon dioxide absorber 28 into the runback pipe 26 and therefrom into the divider valve 24, by the outlet pipe 23 under the membrane 45 of the expiration valve 22. There it increases the force acting on the membrane 45 of the expiration valve 22. The vacuum is also transferred to the check valve 44 in the exhaust system 25 which is thereby closed, and the runback 26 is sealed from the surrounding atmosphere. The vacuum in the connection pipe 15, which is given by the spontaneous activity of the patient, excites an inhalation flow of gases from the rubber bag 17 into the anaesthetical circuit 19. During the outflow of the gases from the rubber bag 17, its walls are deformed under the influence of the pressurized air of the atmosphere, or of the pressure aid of the ventilator regime transferred by the drive pipe 12. Deformation continues until the moment when the rubber bag 17 is emptied and its walls pressed onto itself. At this moment, a higher vacuum occurs in the connection pipe 15, this higher vacuum being transferred by the pipe 14 through the bacteriological filter 47 into the vacuum chamber 13 of the differential pressure indicator 8. The force given by the vacuum and by the effective surface of the membrane 37 overcomes the force of the spring 38 sealing the membrane seat 39. The pressurized air in the control chamber 36 of the valve 4 is equalized with the low or zero pressure in the drive pipe 12 through the conduit 7, the pipe 40, the membrane seat 39, the pressurized chamber 10 and the pipe 11. The pressurized air in the feeding pipe 5 acting in the seat 48 of the valve 4, opens the way into the through flow chamber 35 and therefrom into the inlet pipe 1 of the injector 3. A flow of a mixture of anaesthetical gases arises in the injector 3, the value of the flow being constant and given by the cross section surface of the calibrated opening 31 so as by the vacuum adjusted in the pressure regulator 30. The flow coming from the inlet pipe 1 into the injector 3 is divided in the main channel 49 equipped with the calibrated opening 51, and in the parallel channel 50 equipped with the adjustable throttle element 52. A stream of gases saturated with the vapors of the evaporated escaped anaesthetic streams in the outlet pipe 2 of the injector 3, the stream being conducted in the direction of the pressure gradient through the check valve 16 and the connection pipe 15, and further, on the one hand, through the check valve 46 into the anaesthetical circuit 19 and, on the other hand, into the rubber bag 17. The flow of gases through the injector 3 lasts until the valve 4 remains open, i.e. until a sufficient vacuum lasts in the vacuum chamber 13 of the differential pressure indicator 8. At the moment when the spring 38 closes the membrane seat 39, using its power overbalance, the pipe 40 so as the conduit 7 is filled by a pressure, the maximum value of which is given by the adjustment of the pressure regulator 42. The valve 4 closes the flow of gases into the injector 3 with a delay, the time constant of which is given by the resistance of the conduit 7 and by the capacity of the control chamber 36 of the valve 4. The delay makes possible that the rubber bag 17 is filled until the vacuum in the anaesthetical circuit 19 has already disappeared and the exhalation occurs.

The momentary concentration of the escaped anaesthetics in the mixture of anaesthetical gases is given, under a constant flow of gas through the injector 3, by the momentary flow of liquid phase of the anaesthetic through the capillary tube 53 into the gas stream. The momentary flow of the liquid phase of the anaesthetic is given by the momentary pressure gradient between the inlet pipe one and the outlet pipe 2 of the injector 3. This pressure gradient under a constant flow of gas through the injecor 3, is given by the sizes of the feeding pipe 5, of the main channel 49 and by the position of the adjustable throttle element 52 in the parallel channel 50 of the injector 3. When the adjustable throttle element 52 is minimally open, i.e. when it is closed, the pressure gradient in the injector 3 has its maximum value and the resulting concentration will also have its maximum value. When the adjustable throttle element 52 is maximally opened, the pressure gradient in the injector 3 has its minimum value and also the concentration will be minimal. By varying the aperture of the adjustable throttle element 52 from the maximum to the minimum, the constant flow of gases insignificantly changes what can be compensated by the form of the throttle cross section of the adjustable throttle element 52. The main system of which effects the accuracy of the desired concentration is the the change of the specific mass of the oxygen fraction $FiO_2$ in the nitromonoxide. This is adjustable without respect to the off take of the anaesthetical gases by the automatic gas mixture 54 which feeds the source 6 of constant flow or pressure regulator. This system error can be corrected by adjustment of the desired concentration by means of the adjustable throttle of element 52, with the aid of an alignment chart (nomogram) concerning the change of oxygen concentration in the gas mixture, for example, from a nominal value of $FiO_2$ 0.35 to a value, for example, of 0.7 and the like. The system error of the resulting concentration of the anaesthetic, depending on the level of the liquid anesthetic 55 in the injector 3 which affects the pressure gradient on the capillary tube 53, is negligible in the case when the maximum change of the liquid level, measured from the mouth of the capillary tube 53, excites a negligible change of the pressure gradient in comparison with the minimum pressure gradient in the injector 3 caused by the constant flow of gases, i.e. in the case of the maximum opening of the adjustable throttle 52. Likewise, the system error affecting the resulting concentration of the anaesthetic, depending on the surroudning temperature is negligible.

The exhalation occurring in the anaesthetical circuit causes an increase in pressure which closes the check valve 46 and opens the expiration valve 22, an exhalation flow arising in the outlet pipe 23 of what brings in excess pressure. According to the position of the movable part in the divider valve 24, the excess pressure in it is changed into a runback flow in the runback pipe 26 and into an exhaust flow into the exhaust system 25. Because of the resistance of the pipe 43 in the exhaust system 25 has approximately the same value as the sum of resistances of the runback pipe 26, the carbon dioxide absorber 28, the check valve 29, the connection pipe 15, the expansion of the rubber bag 17 and the drive pipe 12, it is possible to program the value of the instantaneously inhaled reverse volume theoretically from 0-100% which can be done by the position of the movable part of the divider valve 24. The volume of the reverse inhalation will be added to the volume of gases already integrated in the rubber bag 17. In case the volume of gases contained in the rubber bag 17 exceeds its maximum volume given approximately by the volume of the cylinder 18, the excess pressure created in the runback pipe increases, causing the pressurized valve 27 to open and the exceeding volume flows through the pressurized valve 27 away into the surrounding atmosphere. When the exhalation is finished, a further inhalation comes depending on the spontaneous activity of the patient and the operation will be repeated.

In case of a relaxed non-breathing patient, a handoperated ventilator or a controlled mechanical operation is executed. In this case, either a self-expanding bag or wide-joint of a ventilator (not shown in the drawing) is connected to the drive pipe 12. During the inhalation, the excess pressure in the drive pipe 12 increases so that its momentary value is given by the product of the momentary inhalation flow and of the sum of all flow resistances in the inhalation system and by the momentary excess pressure value in the lungs. The walls in the rubber bag 17 are deformed by the difference of the given excess pressure and of the pressure of the rubber bag 17 and thus, the gas is pressed therefrom out through the connection pipe 15 and the check valve 46 into the anaesthetical circuit 19. The excess pressure in the drive pipe 12 is transferred by the pipe 20 into the control chamber 21 of the expiration valve 22. The expiration valve is closed in the inhalation occurs. The excess pressure in the drive pipe 12 is transferred at the same time through the pipe 11 into the pressurized chamber 10 of the differential pressure indicator 8. The excess pressure, diminished by the pressure gradient which is necessary for the deformation of the walls of the rubber bag 17, is transferred from the connection pipe 15 through the pipe 14 into the vacuum chamber 13 of the differential pressure indicator 8. The membrane seat 39 remains closed as the spring 38 presses the membrane 37 on the membrane seat 39. The pipe 40 and the conduit 7 are under the pressure from the pressure regulator 42, the valve 4 remaining closed by the excess pressure in the control chamber 36. The spring 38 counterbalances thereby the power inbalance caused by the pressure difference in the pressurized chamber 10 and in the vacuum chamber 13 of the differential pressure indicator 8 during inhalation when the gas is pressed out from the rubber bag 17. At the moment when the rubber bag 17 is emptied, its walls are pressed onto each other and the excess pressure in the drive pipe 12 suddenly increases, the excess pressure in the connection pipe 15 remaining at the original level. The increased pressure is transferred from the drive pipe 12 through the pipe 11 into the pressurized chamber 10 of the differential pressure indicator 8 where the force acting on the membrane 37 overcomes the force of the spring 38. The membrane 37 makes the membrane seat 39 free, and the excess pressure in the control chamber 36 of the valve 4 is balanced through the conduit 7 and the pipe 40 with the pressurized chamber 10 of the differential pressure indicator 8. As the maximum excess pressure in the drive pipe 12 is given by the maximum inhalation pressure level in the excess pressure of the given drive, that is, to say by the adjustment of the pressure level in the excess pressure drive valve, for example, 8 kPa, the excess pressure in the control chamber 36 of the valve 4, keeping the valve 4 on its opening limit being several times higher, the drop in the excess pressure in the control chamber 36 of the valve 4 to the value of the maximum excess pressure in the drive pipe 12 opens the valve 4. Thereby a constant flow of gases through the injector 3 arises where the gases are saturated by the escaped anaesthetic according to the described mechanism. The constant flow having a resulting concentration of the escaped anaesthetic programmed as described, fills through the check valve 16, the connection pipe 15 wherefrom the rubber bag 17 is filled. A part of the gas will also flow, according to the flow in the drive pipe 12, through the check valve 46 into the anaesthetical circuit 19. At the moment when the flow of gases from the injector 3 fills the rubber bag 17, the pressure drop is caused in the drive pipe 12 because the drive is loaded only by the inhalation pressure in the connection pipe 15. The pressure difference in the pressurized chamber 10 and in the vacuum chamber 13 of the differential pressure indicator 8 is balanced, and the spring 38 presses the membrane 37 in the membrane seat 39. The valve 4 closes the flow of gases with the time constant of the pressures spreading through the conduit 7 into the control chamber 36 of the valve 4. After inhalation, exhalation follows, the mechanics of which is the same as during the spontaneous ventilation of the patient.

The anaesthetical circuit with reverse inhalation equipped with an injector of escaped anaesthetics according to the invention represents a new automatic and autostabilized anaesthetical device, the operation of which is programmed only by oxygen fraction in nitrogen monoxide using and automatic gas mixture 54, by means of the concentration of escaped anaesthetics in the gas mixture, using adjustable throttle element 52 in the injector 3 of the escaped anaesthetics so as by means of a volume return of gases back into the circuit by the adjustment of the divider valve 24. The device distinguished by a simple attendance and by the fact that the transition from the spontaneous regime to a hand-operated ventilator, or to a control ventilation, needs no manual interventions in the breathing circuits. The programed resulting concentration of escaped anaesthetics need no thermal compensation. The dimensions and the mass of the device can be minimal as the circuits of the device are simple, the mass of the injector being many times smaller in comparison with the existing evaporators.

While there has been described a particular embodiment of the invention, it will be apparent to those skilled in the art that variations may be made thereto without departing from the spirit of the invention and the scope of the appended claims.

We claim:

1. An anaesthetical circuit having conduit means for conducting inhalation and exhalation gasses of a patient comprising a source of constant flow having a feeding pipe connected thereto, an injector having an inlet and an outlet, valve means having an inlet and an outlet, said feeding pipe connected from said source of constant flow into said valve means inlet, an inlet pipe connected from the valve means outlet to said injector inlet, a differential pressure indicator having a pressurized chamber and a vacuum chamber defined on opposite sides of a membrane therein, a pressure energy source, a drive pipe, said energy source being connected to said pressurized chamber of said differential pressure indicator from said drive pipe, an opposing pipe and a connection pipe, said opposing pipe connected from said connection pipe into said vacuum chamber which is on the opposing side of the pressurized chamber of said differential pressure indicator, said differential pressure indicator having means for generating a signal indicative of a predetermined pressure differential between said drive pipe and said connection pipe, said valve means being responsive to said signal for opening said valve means, said connection pipe also connecting from the outlet of said injector to said conduit means, a rubber bag connected to said connection pipe and arranged in a cylinder hermetically sealed therearound, said drive pipe also connected into the cylinder, a check valve in said connection pipe upstream of said rubber bag and opposing pipe providing one way flow from said injector, an expiration valve conected to said conduit means and having a control chamber and an outlet pipe a pipe connected from the drive pipe into said control chamber, a distribution valve, into which said outlet pipe is connected, said distribution valve having two branches, one branch of said distribution valve forming an exhaust system, said exhaust system being provided with a check valve providing one-way flow from said distribution valve, the second branch of said distribution valve forming a runback pipe connected to said connection pipe, said runback pipe comprising an overpressure valve connected through a carbon dioxide absorber and then through a check valve to the connection pipe.

2. An anaesthetical circuit as claimed in claim 1, wherein said signal generating means comprises a pressure regulator having a calibrated opening connected to said source of constant flow and a feeding pipe connecting said opening to said pressurized chamber and terminating in an opening adjacent said membrane which closes said opening, and said valve means includes a control chamber connected to said feeding pipe whereby when said feeding pipe opening is closed by said membrane said control chamber is pressurized and said valve means is closed.

3. An anaesthetical circuit as claimed in claim 2 wherein an automatic gas mixer is connected to the source of constant flow.

4. An anaesthetical circuit as claimed in claim 2, wherein the valve means comprises a through-flow chamber, said control chamber, and two membranes, one of said membranes having a smaller effective surface, and the other said membrane having a bigger effective surface, said membranes separating said through-flow chamber of the valve from said control chamber of the valve.

5. An anaesthetical circuit as claimed in claim 4, wherein the differential pressure indicator further comprises a spring in said vacuum chamber biasing said membrane towards said pressurized chamber, a membrane seal being arranged on the center of the membrane, said membrane seal closing the opening of said feeding pipe.

6. An anaesthetical circuit as claimed in claim 5, wherein the exhaust system leading out from the distributor valve includes a pipe the diameter and the length of which forms a resistance, this resistance being comparable with a sum of resistances of the runback pipe, of the carbon dioxide absorber, of the check valve, of the rubber bag and of the drive pipe.

7. An anaesthetical circuit as claimed in claim 1, wherein the injector comprises a main channel having a calibrated opening, an anaesthetic reservoir, a capillary tube extending from adjacent said opening into said reservoir, and a parallel channel being arranged parallelly to the main channel, the parallel channel being provided by an adjustable throttle element.

* * * * *